(12) United States Patent
Van Rens et al.

(10) Patent No.: US 9,711,259 B2
(45) Date of Patent: Jul. 18, 2017

(54) CABLE FOR MEDICAL INSTRUMENTS

(71) Applicant: KONINKLIJKE PHILIPS N.V., Eindhoven (NL)

(72) Inventors: Antonia Cornelis Van Rens, Neunen (NL); Vincent Adrianus Henneken, Utrecht (NL); Ronald Dekker, Valkenswaard (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/360,660

(22) PCT Filed: Nov. 23, 2012

(86) PCT No.: PCT/IB2012/056662
§ 371 (c)(1),
(2) Date: May 27, 2014

(87) PCT Pub. No.: WO2013/080103
PCT Pub. Date: Jun. 6, 2013

(65) Prior Publication Data
US 2014/0318859 A1    Oct. 30, 2014

Related U.S. Application Data

(60) Provisional application No. 61/563,863, filed on Nov. 28, 2011.

(51) Int. Cl.
*H02G 3/00*    (2006.01)
*H01B 7/04*    (2006.01)
(Continued)

(52) U.S. Cl.
CPC ............. *H01B 7/048* (2013.01); *A61B 90/37* (2016.02); *H01B 7/30* (2013.01); *H01B 11/1878* (2013.01);
(Continued)

(58) Field of Classification Search
CPC  H02G 5/066; H01B 11/1873; H01B 11/1808; H01B 11/1834; H01B 11/1856;
(Continued)

(56) References Cited

U.S. PATENT DOCUMENTS 3,676,576 A * 7/1972 Dubernet ............... H01B 7/226
174/113 R
4,936,647 A * 6/1990 Carroll .................. D07B 1/068
174/128.1

(Continued)

FOREIGN PATENT DOCUMENTS

CN       201069672 A    6/2008
FR       2546658 B2 *   7/1985 ............... H01B 7/00
(Continued)

OTHER PUBLICATIONS

Dielectric Phenomena in High Voltage Engineering_1920.*

*Primary Examiner* — Timothy Thompson
*Assistant Examiner* — Guillermo Egoavil (57) ABSTRACT

The invention relates to an electrical cable (100) for exchanging communication signals between two devices, particularly a cable (100) that can be integrated into a catheter or a guidewire (5). The cable (100) comprises at least one pair (120, 130) of differential wires (D1+, D1−, D2+, D2−) that are, during operation, supplied with opposite voltages, thus defining a voltage-neutral plane (VNP) between them. Moreover, the cable (100) comprises at least one set (140) of single-ended wires (S11, S12; S21, S22; S31, S32) that is arranged symmetrically with respect to said voltage-neutral plane (VNP). Optionally a core wire (110) may be used for providing mechanical stability and additional electrical functionality. Electromagnetic disturbances from the differential wires to the single-ended wires (and vice versa) are minimized due to the particular arrangement of wires.

6 Claims, 4 Drawing Sheets

(51) Int. Cl.
*H01B 11/20* (2006.01)
*H01B 7/30* (2006.01)
*H01B 11/18* (2006.01)
*A61B 90/00* (2016.01)
*A61B 5/00* (2006.01)
*A61B 17/22* (2006.01)

(52) U.S. Cl.
CPC ......... *H01B 11/1891* (2013.01); *H01B 11/20* (2013.01); *A61B 5/6851* (2013.01); *A61B 5/6852* (2013.01); *A61B 2017/22042* (2013.01); *A61B 2562/222* (2013.01)

(58) Field of Classification Search
CPC ......... H01B 11/02; H01B 11/04; H01B 11/12; H01B 11/002; H01B 11/06; H01B 7/295; H01B 9/003; H01B 7/0861; H01B 11/1091; H01B 7/0838; H01B 11/1033; H01B 11/10; H01B 7/0009; H01B 7/30; H01B 7/048; H01B 7/185; H01B 7/226; H01B 7/292; H01B 7/1895; H01B 11/20; H01B 11/085; H01B 11/1878; H01B 11/1891; H01B 13/06; A61B 5/6851; A61B 5/6852; A61B 90/37; A61B 2017/22042; A61B 2562/222; H04L 25/0272; H04N 19/00; H04N 21/437; H04N 21/438; H04N 21/43635; G02B 6/4429; G02B 6/4435; G02B 6/4459; G09G 5/006; G09G 5/12; G09G 2320/0252; G09G 2370/04; G09G 2370/10; G09G 2370/047; G09G 2370/12; Y10T 29/49117
USPC .......... 174/27–28, 34, 36, 78, 113 C, 113 R, 174/149 R, 72 R, 70 A, 70 R, 99 R, 103, 174/114 R, 128.1, 126.2; 29/825
See application file for complete search history.

(56) References Cited

U.S. PATENT DOCUMENTS

| | | | |
|---|---|---|---|
| 5,574,250 A * | 11/1996 | Hardie | H01B 11/06 174/102 R |
| 6,614,969 B2 | 9/2003 | Eichelberger et al. | |
| 7,291,786 B2 * | 11/2007 | Matsui | H01B 11/1025 174/102 R |
| 8,143,522 B2 * | 3/2012 | Laudenslager | H01B 11/085 174/110 R |
| 9,357,258 B2 | 5/2016 | Ichimura et al. | |
| 9,491,503 B2 | 11/2016 | Ichimura et al. | |
| 2005/0029006 A1 | 2/2005 | Takahashi et al. | |
| 2006/0258937 A1 | 11/2006 | Daane | |
| 2009/0071691 A1 * | 3/2009 | Clark | H01B 11/06 174/116 |
| 2009/0112128 A1 | 4/2009 | Schiff et al. | |
| 2010/0188567 A1 * | 7/2010 | Ichimura | G09G 5/006 348/441 |
| 2010/0200269 A1 * | 8/2010 | Camp, II | H01B 11/04 174/113 C |
| 2010/0236812 A1 * | 9/2010 | Laudenslager | H01B 11/085 174/113 R |
| 2010/0276174 A1 * | 11/2010 | Grogl | H01B 9/003 174/105 R |
| 2010/0307790 A1 | 12/2010 | Okano | |
| 2010/0329614 A1 * | 12/2010 | Keller | G02B 6/4416 385/101 |
| 2011/0098559 A1 | 4/2011 | Besz et al. | |
| 2011/0100682 A1 | 5/2011 | Nonen et al. | |
| 2011/0220389 A1 | 9/2011 | Huang et al. | |
| 2011/0284287 A1 * | 11/2011 | Glew | G02B 6/4429 174/99 R |
| 2013/0062115 A1 * | 3/2013 | Chang | H02G 3/0481 174/74 R |

FOREIGN PATENT DOCUMENTS

| | | | |
|---|---|---|---|
| JP | H0236131 B2 | | 8/1990 |
| JP | 2002216550 A | * | 8/2002 |
| JP | 2011112905 A | | 6/2011 |
| WO | WO2011092202 | | 8/2011 |

* cited by examiner

VNP

CABLE FOR MEDICAL INSTRUMENTS

CROSS-REFERENCE TO PRIOR APPLICATIONS

This application is the U.S. National Phase application under 35 U.S.C. §371 of International Application Serial No. PCT/IB2012/056662, filed on Nov. 23, 2012, which claims the benefit of U.S. Application Ser. No. 61/563,863, filed on Nov. 28, 2011. These applications are hereby incorporated by reference herein.

FIELD OF THE INVENTION

The invention relates to an electrical cable assembly and a method for exchanging communication signals between two devices, particularly between devices connected by a catheter or guide-wire, and to a medical system comprising such a cable assembly.

BACKGROUND OF THE INVENTION

The WO 2011/092202 A1 discloses a cable assembly for a guide-wire, wherein a core metal wire of said guide-wire is actively used when transferring sensor signals.

SUMMARY OF THE INVENTION

It is an object of the invention to provide means that allow for an improved communication between two devices, particularly devices that are connected by a catheter or a guide-wire in which only little space is available for electrical wires.

This object is achieved by an electrical cable assembly, a method, and a medical system. Preferred embodiments are disclosed in the dependent claims.

According to a first aspect, the invention relates to an electrical cable assembly for exchanging communication signals between two devices, for example between a sensor and a data processing unit. It should be noted that the "exchange" of communication signals shall comprise the cases of both unidirectional and bidirectional communication. The electrical cable assembly comprises the following components:

a) At least one pair of wires, i.e. of electrically conductive (typically metal) lines. As these wires are intended for being supplied with opposite voltages, they will in the following be called "differential wires" for purposes of reference. Moreover, the two differential wires define a "voltage-neutral plane" between them, which is by definition the plane in which voltage becomes (approximately) zero when the two differential wires are supplied with opposite voltages (provided there are no or only negligible electrical potentials in the surroundings). For example, in case of two identical differential wires that are arranged in a mirror-symmetric way, the voltage-neutral plane coincides with said symmetry plane.

b) At least one set of wires that has a configuration which is symmetrical with respect to the aforementioned voltage-neutral plane. With reference to their intended mode of operation, the wires of this set will in the following be called "single-ended wires" for purposes of reference. The set may comprise just one or (preferably) two or more such single-ended wires.

In this context, a "symmetrical configuration of a set of wires" is to be understood in such a sense that characteristic points of each wire, for example their center lines, are arranged in geometrical symmetry. In general, it is however not necessary that the complete wires themselves are symmetric geometrical objects (they may for example have different cross sections), though this will preferably be the case.

It should further be noted that "voltages" are defined as the difference between electrical potentials at two different points. The above statements about voltages (e.g. applied to a wire, or in the voltage-neutral plane) therefore implicitly assume that said voltages are determined with respect to some (common) reference potential, which is typically called "ground" and has, by this definition, zero voltage.

Moreover, the (geometrical position of the) "voltage-neutral plane" is defined with respect to a theoretical situation in which only the two differential wires—and no other components—are supplied with voltages, namely opposite voltages. Once defined, the voltage-neutral plane remains the same even if other voltages are applied to the differential wires and/or if voltages are applied to other components (e.g. the single-ended wires), though the actual voltage in the voltage-neutral plane will then in general no longer be zero.

The cable assembly will typically comprise additional components, for example an outer insulation or housing, an insulation separating the wires from each other and the like. Moreover, the mentioned (differential and single-ended) wires will typically run parallel to each other along the axis of the cable assembly.

According to a second aspect, the invention relates to a method for exchanging communication signals between two devices via an electrical cable assembly. The method comprises the following steps, which may be executed in the listed or any other appropriate order:

a) Supplying (typically high frequency/HF) opposite signal voltages to two "differential wires". As above, the two differential wires define a voltage-neutral plane between them as the plane in which voltage is approximately zero when only the two differential wires are supplied with opposite voltages.

b) Supplying a further signal voltage to a "single-ended wire set" that has a symmetrical configuration with respect to the aforementioned voltage-neutral plane.

The electrical cable assembly and the method are different realizations of the same inventive concept, i.e. the arrangement of wires symmetrical to a voltage-neutral plane. Explanations and definitions provided for one of these realizations are therefore valid for the other realization, too.

The cable assembly and the method defined above have the advantage that they allow for a robust communication between two devices even if the wires inside the connecting cable assembly have to be arranged close to each other. This is because differential wires are provided via which high-speed signals can be transmitted in a differential operation, and additional single-ended wires are provided for low-speed communication via single-ended signals. Electromagnetic disturbances caused by the high-speed differential signals may affect the adjacent single-ended wires. However, due to an arrangement symmetrical with respect to the voltage-neutral plane of the high-speed signals, these disturbances will on the whole compensate each other in the single-ended wires.

The invention further relates to a medical system comprising a first device and a second device that are connected by an electrical cable assembly of the kind described above, thus allowing for an exchange of communication signals according to the above method. The medical system may particularly comprise a catheter or a guide-wire into which said cable assembly is integrated. This is particularly advantageous as there is an increasing demand for a communication with sensors or actuators at the tip of a catheter or a guide-wire, while the space available for wires, on the other hand, is tightly limited.

In the following, various preferred embodiments of the invention will be disclosed that can be realized in combination with the electrical cable assembly, the method, and the medical system defined above.

According to one preferred embodiment, a DC common mode voltage is supplied to the differential wires additionally to the above mentioned opposite signal voltages. If the opposite signal voltages are for example (+V1) and (−V1) and said DC common mode voltage is (V0), then the effective voltage on one differential wire will be (V0+V1) and on the other differential wire (V0−V1). The resulting voltage in the voltage-neutral plane will in this case be equal to (V0) if no voltage is applied to any other component around. If there is more than one pair of differential wires, each pair may independently be supplied with another common mode voltage. Furthermore, the common mode voltage may optionally be a low-frequency signal (e.g. with a frequency lower than about 5 MHz). This way, extra signals e.g. for control can be multiplexed on the differential pair.

The single-ended wires shall have a configuration that is symmetrical with respect to the voltage-neutral plane. This may comprise one or more single-ended wires lying in the voltage-neutral plane itself (thus being symmetrical to themselves). According to a preferred embodiment, there is at least one pair of single-ended wires comprising a first single-ended wire running outside the voltage-neutral plane and a second single-ended wire that is disposed on the opposite side of the voltage-neutral plane at a mirror-symmetric position with respect to said first wire. The two single-ended wires of the aforementioned pair can then commonly be used to convey a single voltage signal (i.e. the same voltage is applied to both wires at an input end of the cable assembly). This is favorable because possible disturbances by differential signals on the differential wires will compensate each other due to the particular symmetrical arrangement of the two single-ended wires.

The at least one pair of differential wires, the at least one set of single-ended wires, and/or one or more wires of this pair or set, respectively, may optionally be surrounded by an electrical shielding. This helps to reduce cross talk between the various wires.

According to another preferred embodiment of the invention, the cable assembly comprises a "core wire" that provides mechanical stability to the cable assembly. The core wire will typically be a metal wire, for example from stainless-steel, though other electrically conductive or non-conductive materials are possible, too. As its name indicates, the "core wire" is preferably disposed at some central position within the cable assembly.

The aforementioned core wire is preferably arranged in the voltage-neutral plane defined by the pair of differential wires. Electromagnetic disturbances in the core wire (if electrically conductive) can then be minimized.

The core wire may optionally be electrically connected to at least one other wire of the cable assembly and/or to a shielding of the cable assembly. If the core wire is electrically conductive, it can hence—additionally to its mechanical function—fulfill an electrical function, for example conveying a common reference voltage ("ground").

In another embodiment, the core wire may have a non-circular cross section (said cross section lying by definition in a plane perpendicular to the axis of the cable assembly).

The cross section may for example be polygonal. A non-circular cross section has the advantage that it helps to arrange and fix other components of the cable assembly at definite locations.

The cable assembly may optionally comprise more than one pair of differential wires to allow for the transfer of a plurality of (differential) signals. In this case, the voltage-neutral planes associated to each pair of differential wires will preferably overlap (i.e. all pairs of differential wires have the same voltage-neutral plane).

The aforementioned two or more pairs of differential wires are preferably arranged at a maximal distance with respect to each other, wherein the possible maximum is of course limited by the given size of the cable assembly. Arranging pairs of differential wires as far away from each other as possible has the advantage that mutual cross talk is minimized.

When two or more pairs of differential wires are provided, the above mentioned core wire is preferably arranged between them, thus providing an additional shielding against cross talk.

According to a preferred embodiment, the cable assembly is geometrically symmetric with respect to the voltage-neutral plane defined by the pair of differential wires. This means that the geometrical shape and arrangement of all components of the cable assembly (differential wires, single-ended wires, shieldings, insulation material etc.) is symmetric. Accordingly, the geometrical symmetry comprises both the general arrangement of wire-centers as well as the cross sections of the wires. Additionally, the symmetry may comprise also the materials of the respective components. Thus an optimal balance with respect to the voltage-neutral plane can be achieved which helps to minimize the overall effects of electromagnetic disturbances from (and on) the differential wires.

The opposite voltage signals (e.g. (+V1) and (−V1)) that are supplied to the differential wires and/or the further signal voltages that are supplied to the single-ended wires are typically AC signals (i.e. the sign of V1 changes repetitively). More particularly, the opposite voltages signals on the differential wires are preferably high-speed signals with a frequency higher than about 20 MHz. The further signal voltages on the single-ended wires are preferably low-speed signals with a frequency lower than about 5 MHz. Thus optimal ranges for the respective signals can be exploited.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

Diagnosis and treatment in minimally invasive healthcare procedures may be improved by integrating imaging and sensing devices at the tip of interventional instruments—such as catheters and guide-wires. However, the very limited size of these instruments poses an important challenge in integrating the required functionality. Micro-machining (MEMS) sensors can be integrated with ASIC technology and enable advanced imaging and/or sensing functionality in a very small area. The related trend is that an increasing amount of data needs to be transferred from the tip of the instrument to the external equipment.

Figure 1:
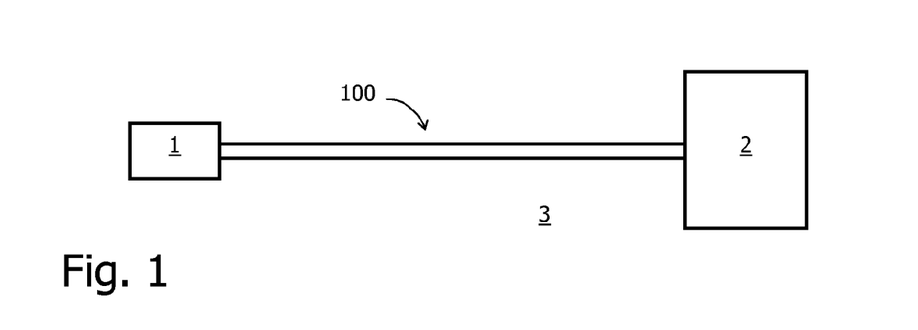
FIG. 1 schematically shows the application of a cable assembly in a medical system.

FIG. 1 schematically shows the use of a cable assembly 100, running for example through a catheter or a guide-wire, for the communication between devices 1 at the tip (in-vivo) and external equipment 2 (ex-vivo). This interconnect has to transfer the signals in an effective way, which basically means: requiring little hardware at the tip, a low number of (miniaturized) wires, while maintaining signal integrity. A low wire-count is important due to the limited space available to route the wires. A typical size of the inner diameter of a guide-wire is about 260 µm. This also restricts the area for in-vivo functionality.

Hence there is a need for a high-speed electrical cable assembly that is optimized for usage in a standard guide-wire. The assembly typically has a length of 2 meters and a diameter of about 250 µm. Due to the frequencies involved (e.g. 10 MHz-500 MHz), the cable characteristics will be determined by transmission line effects. Cable losses are dominated by wiring resistances which are high due to the small diameter and the long length, while frequency dependent losses (skin- and proximity-effect) worsen the situation for high frequencies.

Figure 2:
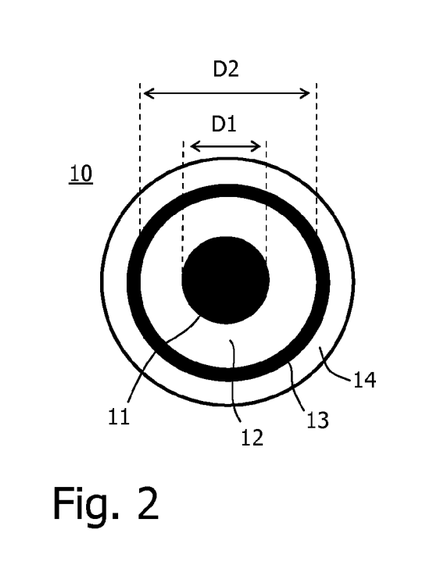
FIG. 2 shows a cross section through a conventional coax cable assembly.

FIG. 2 shows a cross-section of a standard coax cable assembly 10 as it is used in standard transmission lines. Typically, the signal current flows through the conducting core 11 while the return current (and no other current!) flows via the shield 13, which are separated by an insulation 12. The final layer of the coax cable assembly is a non-conducting sheath 14 which prevents an electric current path between the shield and external components.

If the shielding is sufficiently thick, the generated electromagnetic (EM) field can be captured inside the coax cable assembly 10, and no EM field is generated outside the cable assembly. The characteristic impedance of the coax is determined by the dielectric constant of the dielectric medium ($\epsilon_R$) and the dimensions of core and dielectric medium, in formula:

$$Z_0 = \frac{120}{2\sqrt{\epsilon_R}} \cdot \ln\left(\frac{D2}{D1}\right)$$

with D1 being the diameter of the core 11, D2 the inner diameter of the shield 13.

The diameter D1 of the core 11 and the electrical resistivity ($\rho$) of the used material determine the core series resistance. In case of a copper core with a diameter of D1=30 µm, the low-frequency core resistance R is given by:

$$R \approx \frac{L \cdot \rho}{\frac{\pi}{4} \cdot D1^2} \approx L[m] \cdot \frac{21400}{D1^2[\mu m]} \approx L[m] \cdot 24 \Omega$$

Due to the skin effect, the effective series resistance increases at high frequencies. At 125 MHz, the series resistance has doubled, and at 500 MHz the series resistance is about four times higher than at DC.

The signal attenuation of the coax cable assembly 10 is related to the ratio of the above characteristic impedance ($Z_0$) and the core losses (R). The presented formulas show that miniaturization of coax cables results into degradation of electrical performance. Furthermore, the electrical performance of a coax cable assembly is determined by the quality of the shield (13). The series resistance $R_S$ of the conductive shield must be much smaller than the characteristic impedance of the cable ($R_S \ll Z_0$) to avoid attenuation of the signal. Furthermore, voltage drop over the shield which causes electromagnetic radiation outside the coax cable assembly is avoided. In case of a miniaturized cable assembly, the diameter D2 is small and therefore the thickness of the shield should be relatively high. As a rule of thumb, the shield must have a thickness larger than 3δ with δ being the skin depth of the material (3δ=20 µm for copper at a frequency of 100 MHz) to be effective in blocking an electromagnetic field; this holds for both external and internal EM fields.

Figure 3:
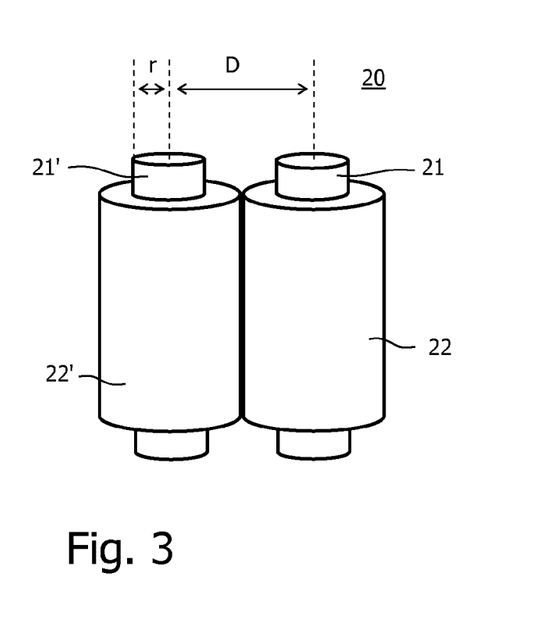
FIG. 3 shows a side view of an unshielded twisted pair of wires.

FIG. 3 shows a side view of an unshielded (twisted) pair 20 of wires 21, 21' surrounded by an insulation 22, 22'. Typically unshielded twisted pairs are used to transfer differential signals, i.e. both wires 21, 21' transfer identical signals but with inverse polarity. Therefore the net common-mode current is zero, and no net current is flowing into a ground or other return node.

Due to the usage of differential signals over closely aligned wires, the overall electromagnetic radiation (EMI) generated by the cable assembly 20 is relatively low and the cable assembly has a moderate susceptibility to external electromagnetic radiation (EMS). Twisting the wires can improve the EMI and EMS performance considerably.

The characteristic impedance of a pair of two parallel conducting wires in an infinitely large and homogeneous dielectric medium is determined by the dielectric constant $\epsilon_R$ of the dielectric medium, the radius r of the conducting wires, and the distance D between the wires:

$$Z_0 = \frac{120}{\sqrt{\epsilon_R}} \cdot \ln\left(\frac{D}{r}\right)$$

The characteristic impedance of a twisted pair typically is higher than the characteristic impedance of a coax, which has advantages when miniaturizing. However, it is important to realize that the formula assumes a fixed dielectric medium around the two core wires. When used inside a guide-wire, this is not the case; the (twisted) pair will be surrounded with other conductive wires. Furthermore, the cable assembly could be surrounded by air ($\in_R=1$) or by water ($\in_R=80$) or by a mix of the two. The guide-wire surrounding the cable assembly could be made from a conductive material (e.g. stainless steel) or by a non-conductive material. These dependencies cause that the twisted pair will have different impedance characteristics depending on its environment, which makes an un-shielded cable assembly difficult to use for transfer of high-frequency signals in guide-wires.

In view of the above background, it was the object of the present invention to provide an electrical high-speed cable assembly that can be used in a standard guide-wire. A particular problem in this application is that the available space to route wires inside a guide-wire is very limited. The inner diameter of the guide-wire typically may be about 260 μm, wherein an important part of this area is already occupied by a steel core wire which is placed inside the guide-wire to give it its mechanical properties.

The solution proposed by the present invention comprises an electrical high-speed cable assembly that can be used in a standard guide-wire, which integrates the stainless steel core wire such that it contributes to the electrical functionality of the assembly. Furthermore, the cable assembly combines high-speed differential signal wires and low-frequency single-ended signaling wires in such a way that electromagnetic cross talk of both types of signal wires has little influence on the performance of the other. This means that signal integrity can be maintained, even if the wires are gathered in a very small area. This way the limited space available in a guide-wire (or small catheter) is used in an optimal way.

Figure 4:
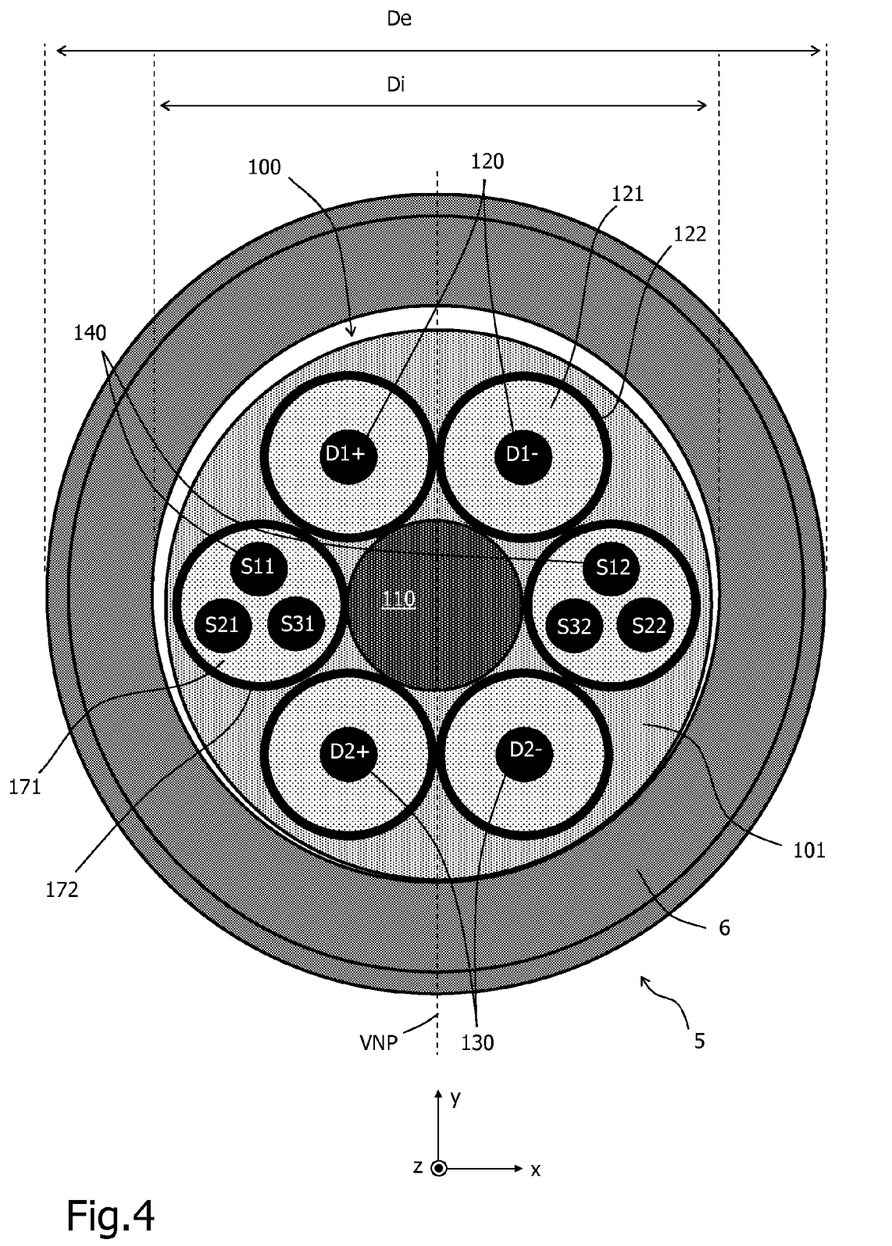
FIG. 4 shows a schematic cross section through a guide-wire comprising a cable assembly according to the invention.

FIG. 4 shows a cross-section through an embodiment of the proposed cable assembly 100 when being located within the tube 6 of a guide wire 5. The exterior diameter $D_e$ of the guide wire tube may for example be about 350 μm, its inner diameter $D_i$ about 260 μm. The diameter of the cable assembly 100 is such that it can be placed inside the (standard) guide-wire tube 5.

The electrical cable assembly 100 comprises the following components:

A first pair 120 of "differential wires" (D1+) and (D1−) that each are embedded in an insulation 121 (low K dielectric material) and surrounded by an electrically conductive shielding 122, for example a gold plating. The dielectric constant of the insulation 121 must be low to maximize the characteristic impedance of the differential wires. The two differential wires define a "voltage-neutral plane" VNP as the plane in which voltage becomes zero if both wires (D1+) and (D1−) are supplied with HF-voltages of opposite polarity. As the differential wires (D1+) and (D1−) are identical in geometry and material, the voltage-neutral plane VNP corresponds to the symmetry plane in the shown case.

A second pair 130 of differential wires (D2+) and (D2−) that are insulated and shielded as the first pair. The second wires (D2+) and (D2−) are arranged such that their voltage-neutral plane coincides with the aforementioned voltage-neutral plane VNP.

A first pair 140 of "single-ended wires" S11 and S12 that are disposed symmetrically with respect to the voltage-neutral plane VNP.

A second pair of "single-ended wires" S21 and S22 that are disposed symmetrically with respect to the voltage-neutral plane VNP.

A third pair of "single-ended wires" S31 and S32 that are disposed symmetrically with respect to the voltage-neutral plane VNP.

An insulation 171 embedding the first single-ended wires S11, S21, S31 of the aforementioned pairs and a shielding 172 surrounding them. This shielding is preferred but not absolutely required.

An insulation embedding the second single-ended wires S12, S22, S32 of the aforementioned pairs and an optional shielding surrounding them.

A (stainless) steel, preferably with a low magnetic permeability, core wire 110 with a circular cross-section to aid the desired mechanical properties of the guide-wire such as uniform bendability, axial stiffness, and torqueability.

A filler material 101 providing an insulating sheath which prevents electrical current to flow outside the assembly and inside the human body.

The high degree of symmetry of the described cable assembly 100 is beneficial for the uniformity of its bending behavior and beneficial for electromagnetic characteristics.

It should be noted that the geometrical position of the voltage-neutral plane VNP is defined as the plane in which voltage becomes zero if both differential wires (D1+) and (D1−) are supplied with voltages of opposite polarity and no other component is connected to any voltage. If common mode signals (DC or LF) are however applied to the differential wires and/or if single-ended signals (DC or LF) are provided to the single-ended wires and/or to the core wire, this potential may impact the potential of the voltage-neutral plane VPN as well as the potential of the environment. In general, the voltage in the voltage-neutral plane VPN will then no longer be zero (which is no contradiction because the conditions no longer correspond to those of the definition of the voltage-neutral plane). However, due to the symmetry of the wire positions (differential and single-ended), the potential change on a position (x,y) will be the same as the potential change on the mirrored position (−x,y), where x=0 is the position of the voltage-neutral plane VPN. As the wires of a differential pair are located at some position ($-x_{wd},y$) and ($x_{wd},y$), this potential change will not impact the differential signal. Something similar holds for the pairs of single-ended wires. Due to symmetry, the combined wires will not suffer from the signals on the differential wires (single-ended wires could however disturb other single-ended wires, that is why it is preferred to limit signals on these wires to DC and LF signals).

The core wire 110 has been integrated in the assembly and has a triple function: It gives the guide-wire its required mechanical properties, it provides the electrical connection of the shielding, and it simplifies correct alignment of the signal wires. In particular, the steel core connection serves as the common reference (e.g. ground GND).

As described above, the assembly typically is equipped with two pairs 120, 130 of "high-speed differential wires" (D1+, D1−; D2+, D2−) that are optimized to transfer high-speed differential signals, and with a number of "low-speed single-ended wires" (S11, S12; S21, S22; S31, S32) that are used in pairs and use single-ended signaling.

The two high-speed differential wire pairs 120, 130 are placed parallel to each other at a maximum distance to minimize crosstalk. The low-frequency signal wires (S11, S12; S21, S22; S31, S32) and the core wire 110 are physically placed between the high-speed differential wire pairs and contribute to the shielding of the EM-fields of the high-frequency signals.

If, and as, the low-frequency wires (S11, S12; S21, S22; S31, S32) contribute to the shielding, eddy currents are induced in the low-frequency signal wires. By combining two low-speed signal wires that induce equal magnitude but opposite sign EM currents (e.g. S11 and S12; S21 and S22; S31 and S32), the net EM energy in the paired wires will be close to zero. This means that external circuits that are connected to the (paired) signal wires will experience little EM interference, thus maintaining the signal integrity.

Eddy currents that are introduced in the steel core automatically do have a net value of zero due to the location of the steel relative to the high-speed and low-speed signal wires.

The cancellation of EM energy also works the other way around: in case the paired low-frequency signal wires (S11, S12; S21, S22; S31, S32) generate EM energy (which is less likely), this will have little impact on the quality of the differential high-frequency signals in the differential wires (D1+, D1−; D2+, D2−) as this energy will result in common-mode interference only.

The high-frequency differential wires (D1+, D1−; D2+, D2−) are equipped with a highly conductive coax-like shielding 122. The low-speed single-ended wires (S11, S12; S21, S22; S31, S32) are collected in groups and are potentially given a shield 172 as well. Because of the described cancellation of EM energy, it is possible to connect all conducting shields 122, 172 to one signal node, for example the core wire 110. This minimizes the area consumed by the cable assembly.

The in-vivo functionality at the tip of the guide-wire or catheter typically comprises mainly sensors and actuators integrated with the driving and/or read-out electronics, gathered in one or more ASICs. Due to the limited area, there is little space available to do extensive supply decoupling. Therefore, it is attractive to choose differential circuit topologies that avoid signal dependent currents in supply and ground and therefore avoid high-frequency disturbance of the local supplies.

Due to the mechanical distance between in-vivo and ex-vivo functionality in relation to the used signal frequencies, the cable characteristics are determined by transmission line effects. To guarantee the required differential behavior, it is important that both signal wires of a pair "see" the same environment and therefore identical characteristic impedance. Furthermore, it is important that both signal wires equally suffer from potential electromagnetic disturbances. This requires a strong symmetry in the cable assembly, which is for example provided by the described embodiment of the cable assembly 100.

Figure 5:
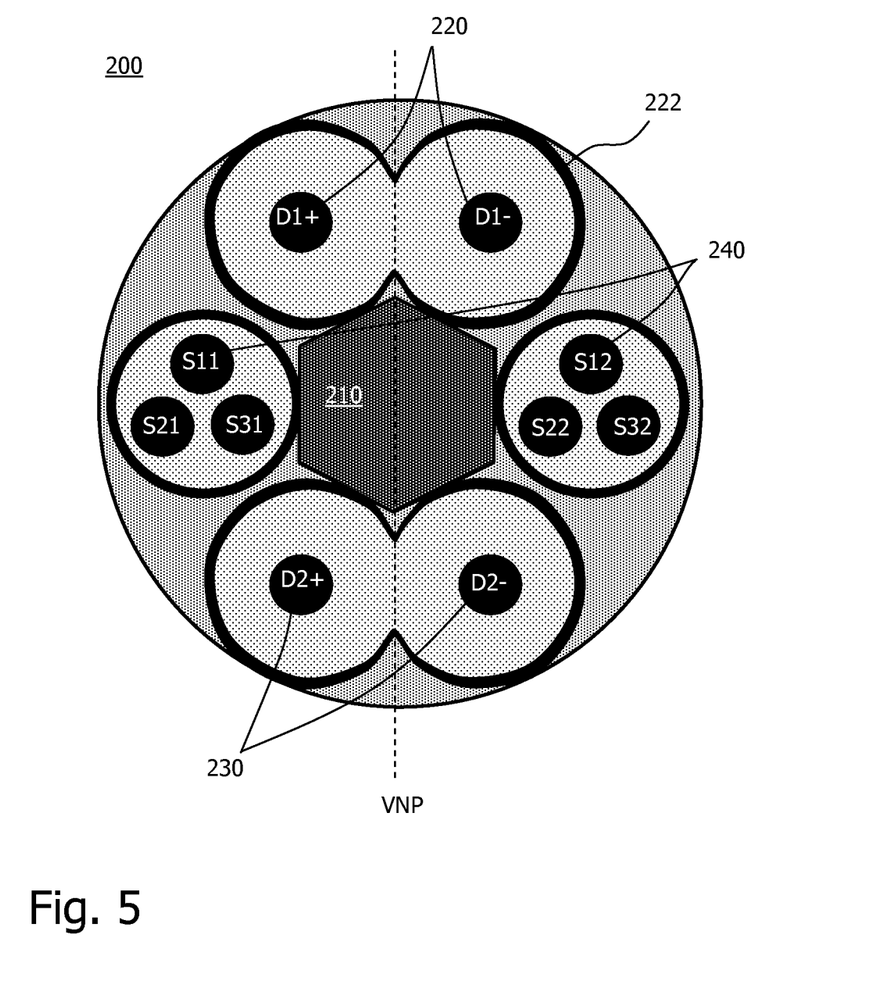
FIG. 5 shows a cross section through an alternative cable assembly according to the invention in which the core wire has a noncircular cross-section.

In the cable assembly embodiment of FIG. 4, the shape of the core wire 110 is round. FIG. 5 shows a cross section through a second embodiment of a cable assembly 200 in which the steel core wire 210 has been given a (here polygonal) pre-shape to ease the alignment of the signal wires. A pre-shape can for example be realized by roll forming or grinding. Another difference of the cable assembly 200 is that the two wires in each pair 220, 230 of differential wires are surrounded by a common shielding 222.

The described cable assemblies 100, 200 allow transfer of two high-speed signals using differential signaling. In comparison with standard coax-cables, the assembly uses thin shields, mutually and through the core wire connected to the in-vivo and ex-vivo devices. As the individual shields are shorted to the core wire, there is no need to connect the individual shields to external components and it is possible to realize the shield with e.g. gold or copper plating.

The two differential wires of a high-speed pair (120, 130; 220, 230) may be placed in a single shield 222 (FIG. 5) or may be given two shields 122 (FIG. 4). Using a single shield may be beneficial from an area point of view; using a shield between the wires may give better defined characteristic impedance due to a better controlled distance between the two wires and between the wires and the shield.

Choosing the thickness of the shields is compromising between EM characteristics and area. A reasonable thickness could be 5-10 µm (=1-2δ, with δ being the skin depth of copper) if used at a signal frequency 100 MHz. This thickness gives the signal wires defined characteristic impedance and reduces the EM radiation outside the shield to some extent. It should be noted that using differential signaling already reduces the net EM field considerably.

In the application, the non-ferromagnetic stainless steel core wire 110, 210 has a galvanic connection to an electrical common voltage node (e.g. ground). Though stainless steel has a relative high electrical resistivity, the overall resistance of the connection is relatively low due to the high conductivity of the shorted shields. Furthermore, the net current flowing through the core wire is low due to the differential behavior of the high-speed signals.

The cable assemblies 100, 200 integrate a number of low-frequency single-ended wires (S11, S12; S21, S22; S31, S32) to transfer low-frequency signals such as power supplies or bias voltages. In the shown embodiments, there are three single-ended low-frequency signal pairs. The core diameter of these single-ended wires (S11, S12; S21, S22; S31, S32) will potentially be somewhat larger to reduce series resistance to be able to drive larger (supply) currents. The distance between the low-frequency single-ended wires and the characteristics of the insulating medium is less critical due to their low-frequency nature.

Figure 6:
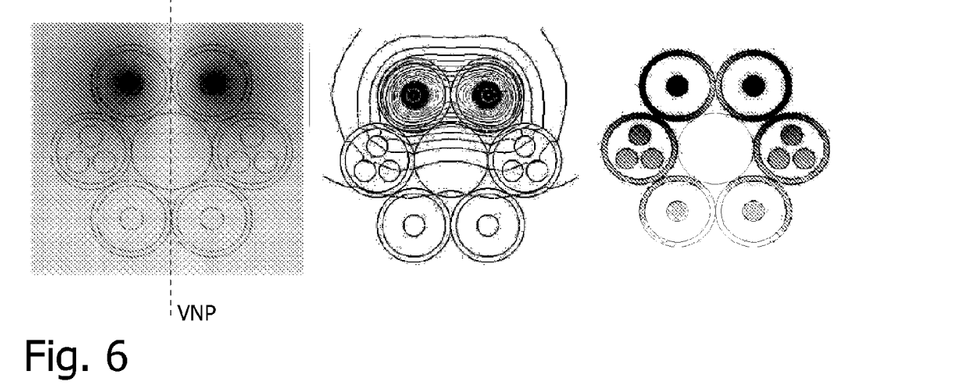
FIG. 6 illustrates the electrical field (left), the magnetic flux (middle), and the induced current density (right) simulated for a cable assembly according to the invention when a differential current with a frequency of 5 MHz is driven through the top pair of the differential wires.
Figure 7:
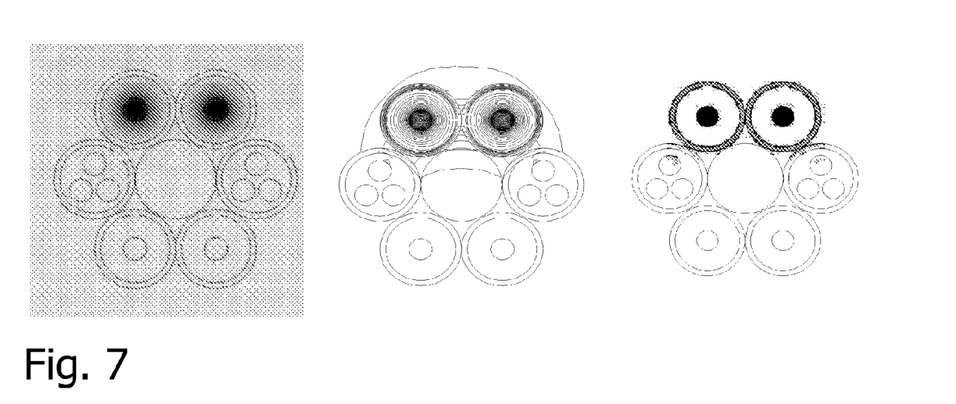
FIG. 7 illustrates the electrical field (left), the magnetic flux (middle), and the induced current density (right) simulated for a cable assembly according to the invention when a differential current with a frequency of 100 MHz is driven through the top pair of differential wires.
Figure 8:
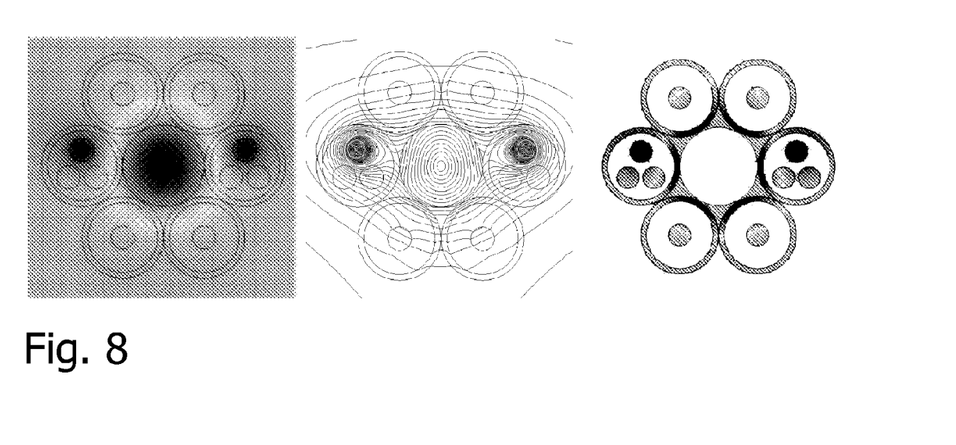
FIG. 8 illustrates the electrical field (left), the magnetic flux (middle), and the induced current density (right) simulated for a cable assembly according to the invention when a single ended current with a frequency of 5 MHz is driven through one pair of the single-ended wires.

FIGS. 6-8 show results of simulations for the proposed cable assembly 100 (FIG. 4).

Each Figure shows the electrical field (left diagram, surface plot), the magnetic flux (center diagram, contour plot), and induced current density (right diagram, surface plot). The dimensions of the used structures result in a cable assembly with a diameter of 252 µm. The shielding layers (thickness 6 µm) as well as the signal wires were assumed to be made out of copper, the centre core wire to be made out of non-ferromagnetic steel. The simulation assumes an infinitely long cable assembly with currents flowing in a direction perpendicular to the drawing plane.

In the first simulation shown in FIG. 6, the pair of upper differential wires (D1+, D1− in FIG. 4) is driven with a differential current with a frequency of 5 MHz. No external current is driven towards the remaining structures.

In the second simulation shown in FIG. 7, the pair of upper differential wires (D1+, D1− in FIG. 4) is driven with a differential current with a frequency of 100 MHz. No external current is driven towards the remaining structures.

In the third simulation shown in FIG. 8, a current is driven to a pair of low-frequency single-ended wires (here the pair 140 of wires S11 and S21 of FIG. 4). The simulation is run for a signal with a frequency of 5 MHz, which is considered to be the highest frequency potentially used on a single-ended wire.

It should be noted that the electromagnetic behavior of the cable assembly is simplified in the simulations by assuming that currents will flow in the direction perpendicular to the drawing plane only (i.e. along the cable axis).

FIG. 6 shows that a medium-frequency (5 MHz) electromagnetic field (EM field) can penetrate through the thin shield. The Figure also shows that induction currents are generated in the low-frequency single-ended wires, which indicates that these wires contribute to EM shielding and prevent that the EM field reaches the second high-speed differential wire pair.

As the low-frequency single-ended wires are used in pairs—a pair is formed by two wires that are located axial-symmetrical with respect to the electrically neutral line VPN—the induced currents have the same magnitude but opposite phase. This means that the net EM disturbance on the paired connection is minimized. Phrased differently, the induced current will flow around in the cable and will not leave the cable and therefore will not interfere with the external components and currents.

From FIG. 6 it is visible that the EM-field can penetrate the shield, which means that for these (relatively low) frequencies, the characteristic impedance is not defined very well and changes with the environment the cable assembly is being used in (e.g. water instead of air).

When used at a higher signal frequency (e.g. 100 MHz as shown in FIG. 7), the shield is more effective, which means that the characteristic impedance of the high-speed differential wire pair is better defined and is less sensitive to environmental changes (e.g. usage in water versus air). This means that the cable assembly probably is best used at high data-rates and signal frequencies.

FIG. 8 shows the results of a simulation that drives single-ended signaling current through a low-frequency single-ended wire pair (return current flows via the core-wire). The EM field penetrates through the thin shield and is capable of reaching the differential wire pairs. However, due to the location of the single-ended wires pair relative to differential wires pair, the EM energy only will result in common-mode energy which will hardly impact the differential signaling of the cable assembly.

It should be noted that the high-speed differential wire pairs remain sensitive to interference from low-to-medium frequency external EM-fields. By using the two high speed differential pairs (120, 130 in FIG. 4) in anti-parallel, an important part of the interference can be cancelled.

In summary, the invention presents an electrical high-speed cable assembly that is optimized for usage in guide-wires. The assembly integrates a steel core wire to give the guide-wire the required mechanical properties. In the proposed assembly this core wire serves multiple purposes; next to the mechanical function, it also contributes to the electrical functionality of the cable assembly and it assists proper alignment of the signal wires. Furthermore, the cable assembly combines high-speed differential signal wires and low-frequency single-ended signaling wires in such a way that electromagnetic (EM) cross talk of both types of signal wires has little influence on the performance of the other. This means that signal integrity can be maintained. The invention is especially useful in communication links with minimally invasive instrumentation, e.g. ultrasound imaging or in-body sensors (flow, pressure, temperature) from a guide-wire.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An electrical high speed cable assembly for exchanging communication signals between two devices, comprising:
    a) at least one pair of "differential wires" which define a voltage-neutral plane between them as the plane in which voltage is approximately zero when only the differential wires are supplied with opposite voltages;
    b) at least one set of "single-ended wires" having a configuration that is symmetrical with respect to the voltage-neutral plane; and
    c) a core wire is comprised of metal that provides mechanical stability;
wherein the core wire has a noncircular cross-section.

2. The electrical high speed cable assembly according to claim 1,
    wherein the set of single-ended wires comprises at least one pair of single-ended wires that are arranged symmetrically with respect to the voltage-neutral plane, the at least one pair of single ended wires having the same magnitude and opposite phase.

3. The electrical high speed cable assembly according to claim 1,
    wherein the pair of differential wires, the set of single-ended wires, and/or wires thereof are surrounded by an electrical shielding.

4. The electrical high speed cable assembly according to claim 1,
    wherein the core wire is arranged in the voltage-neutral plane.

5. The electrical high speed cable assembly according to claim 1,
    wherein the core wire is electrically connected to at least one other wire and/or to a shielding of the cable assembly.

6. A medical system comprising a catheter or a guide wire, said system comprising a first device and a second device that are connected by an electrical high speed cable assembly for exchanging communication signals between the first device and the second device, the assembly comprising:
    a) at least one pair of "differential wires" which define a voltage-neutral plane between them as the plane in which voltage is approximately zero when only the differential wires are supplied with opposite voltages;
    b) at least one set of "single-ended wires" having a configuration that is symmetrical with respect to the voltage-neutral plane; and
    c) a core wire that provides mechanical stability.

* * * * *